United States Patent
Jenko et al.

(10) Patent No.: US 7,923,570 B2
(45) Date of Patent: Apr. 12, 2011

(54) PROCESS FOR THE PREPARATION OF CRYSTALLINE PERINDOPRIL

(75) Inventors: Branko Jenko, Ig (SI); Anton Copar, Smartno pri Ltiji (SI)

(73) Assignee: Lek Pharmaceuticals, D.D., Ljubljana (SL)

( * ) Notice: Subject to any disclaimer, the term of this patent is extended or adjusted under 35 U.S.C. 154(b) by 378 days.

(21) Appl. No.: 11/996,438

(22) PCT Filed: Jul. 24, 2006

(86) PCT No.: PCT/EP2006/007258
§ 371 (c)(1),
(2), (4) Date: Jul. 18, 2008

(87) PCT Pub. No.: WO2007/017087
PCT Pub. Date: Feb. 15, 2007

(65) Prior Publication Data
US 2008/0306135 A1    Dec. 11, 2008

(30) Foreign Application Priority Data
Jul. 25, 2005    (SI) .................................. P200500214

(51) Int. Cl.
*C07D 209/04*    (2006.01)

(52) U.S. Cl. ...................................................... 548/492

(58) Field of Classification Search .................... 548/492
See application file for complete search history.

(56) References Cited

FOREIGN PATENT DOCUMENTS

| WO | 2005019173 | 3/2005 |
|----|------------|--------|
| WO | 2005068425 | 7/2005 |

OTHER PUBLICATIONS

Morissette et al. Advanced Drug Delivery Reviews 2004, 56, 275-300.*
Vippagunta et al., abstract, Vippagunta, Sudha R. "Crystalline Solids." Advanced Drug Delivery Reviews 48(2001): 3-26.*
A. Maureen Rouhi, The Right Stuff: From research and development to the clinic, getting drug crystals right is full of pitfalls, Chem. & Eng. News, 81(8), Feb. 24, 2003, 32-35.*
Brittain, H.G. (Polymorphism in Pharmaceutical Solids—Drugs and the Pharmaceutical Sciences, V. 95; New York Marcel Dekker, Inc., 1999), p. 236.*
Vincent M et, al: "Synthesis and Ace Inhibitory Activity of the Stereoisomers of Perindopril (S 9490) and Perindoprilate" (S 9780), Drug Design and Discovery, Harwood Academic Publishers GMBH, vol. 9, No. 1, 1992, pp. 11-28.

* cited by examiner

*Primary Examiner* — Yong Chu
*Assistant Examiner* — Samantha L Shterengarts
(74) *Attorney, Agent, or Firm* — Arent Fox LLP

(57) ABSTRACT

The present invention relates to a new process for the preparation of crystalline perindopril. The present invention also relates to new alkyl ammonium salts of perindopril and the processes for the preparation thereof.

3 Claims, 2 Drawing Sheets

PROCESS FOR THE PREPARATION OF CRYSTALLINE PERINDOPRIL

This application is the National stage of International Application No PCT/EP2006/007258, filed on Jul. 26, 2006, which claims benefit under 35 U.S.C §119 (e) to Slovenian patent application P200500214 filed on Jul. 25, 2005, the contents of both are incorporated herein by reference in their entirety.

The present invention relates to a new process for the preparation of high pure crystalline perindopril. The present invention also relates to new alkyl ammonium salts of perindopril.

Perindopril and its pharmaceutically acceptable salts are known as angiontensin converting enzyme inhibitors and are used in the treatment of cardiovascular diseases, especially in the treatment of hypertension and heart failure. Perindopril is chemically known as (2S,3aS,7aS)-((2-(1-(ethoxycarbonyl)-(S)-butylamino)-(S)-propionyl)octahydro-indole-2-carboxylic acid and can be represented by formula (I).

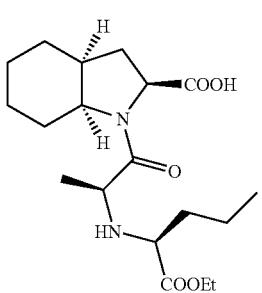

Perindopril was first disclosed in EP 0049658 B1 and U.S. Pat. No. 4,508,729 as optically pure S,S,S,S,S isomer and in the form of sodium salt. Numerous later patents and patent applications, such as EP 0308341 B1, EP 1279665 A1, WO 2004/099236 describe various processes for the preparation of perindopril.

Perindopril in a non-salted form is an oily, amorphous or hardly crystalline material depending on the process used for the preparation thereof and the presence of impurities. Hitherto only tert-butylamine salt of perindopril, i.e. perindopril erbumine, firstly disclosed in EP 0308341, has enough good crystalline properties to be used for pharmaceutical purposes (i.e. having well defined and stable physical properties). EP 1296947 B1, EP 1294689 A and EP 1296948 B1 disclose α, β and γ crystalline forms of perindopril erbumine, respectively. WO 2004/113293 disclose δ and ε crystalline forms of perindopril erbumine and WO 2004/046172 disclose a monohydrate of perindopril erbumine.

One can also mention prior art documents related to processes for the preparation of pure perindopril erbumine. For example, WO 2005/019173 describes a process for the preparation of pure perindopril erbumine by extracting aqueous solution of perindopril or its salt with suitable organic solvent at pH from 4.0 to 6.5, followed by separating of organic layer and preparing perindopril erbumine by adding tert-butylamine. However, neither this nor any other published prior art document discloses isolation of crystalline perindopril.

Crystalline perindopril and a process for the preparation thereof is disclosed only in patent application PCT/EP2005/00283. According to the process described in said application, crude perindopril is purified by column filtration. However, the use of column filtration is not convenient for processes performed at the industrial scale.

There is therefore a need for developing improved process for the preparation of crystalline perindopril, usable at the industrial scale and allowing to obtain a high pure final product.

The present invention provides a new process for the preparation of crystalline perindopril via new alkyl ammonium salts of perindopril selected from the group consisting of tert-octylammonium salt of perindopril and neopentylammonium salt of perindopril.

The process of the present invention avoids the drawbacks associated with the process known from the prior art, i.e. the use of column filtration, allowing the preparation of crystalline perindopril at an industrial scale and provides crystalline perindopril of formula (I) with a high chromatographic purity.

A first object of the present invention is related to a process for the preparation of crystalline perindopril, preferably having at least 99% of chromatographic purity, comprising the steps of:
 (a) transforming crude perindopril to a perindopril alkyl ammonium salt selected from the group consisting of perindopril tert-octylammonium salt and perindopril neopentylammonium salt, and
 (b) regenerating perindopril from said perindopril alkyl ammonium salts and isolating crystalline perindopril.

In a preferred process according to the present invention, step (a) comprises the following sub-steps of:
 (a1) dissolving crude perindopril in an organic solvent, or in a mixture of organic solvents, or in a mixture of organic solvent and water,
 (a2) adding an amine selected from the group consisting of tert-octylamine and neopentylamine,
 (a3) optionally cooling the obtained solution to temperature below 40° C., and
 (a4) separating the obtained precipitate.

The organic solvent used in sub-step (a1) is for example selected from the group consisting of esters, nitrites, ketones, ethers, chlorinated hydrogencarbons and $C_4$-$C_8$ alkyl alcohols or a mixture thereof. Preferred solvents used in sub-step (a1) are esters or nitrites. More preferred solvents used in sub-step (a1) are isopropyl acetate, ethyl acetate or acetonitrile.

The most preferred solvent used in sub-step (a1) for the preparation of perindopril tert-octylammonium salt is acetonitrile, especially acetonitrile comprising a small amount of water, preferably up to 5% (w/w) of water, more preferably from about 0.5 to about 3.5% of water.

The most preferred solvent used in sub-step (a1) for the preparation of perindopril neopentylammonium salt is ethyl acetate.

The solution obtained from sub-step (a1) can optionally be filtered in order to remove potential insoluble impurities before adding the amine in sub-step (a2).

The amine used in step (a2) can be added in one portion, in more portions or drop-wise in a neat form or dissolved form, preferably at temperature from about −20° C. to reflux temperature of used organic solvent. Preferably the amine is added at temperature from about 30° C. to about 40° C. Amines are added in excess from about 1:1.1 to about 1:5 equivalents, preferably from about 1:1.5 to about 1:3 equivalents.

In sub-step (a3), the solution is preferably cooled to a temperature below 20° C. More preferably the solution comprising tert-octylamine is cooled below 10° C., most preferably to 0° C.

More preferably the solution comprising neopentylamine is cooled below 0° C., most preferably to −10° C.

Preferably in sub-step (a4) precipitate is separated by filtration. A filtration of precipitate in sub-step (a4) is preferably carried out from about 0.5 to about 24 hours after the completion of sub-step (a3), more preferably from about 2 to about 6 hours after the completion of sub-step (a3).

The precipitate obtained from sub-step (a4) can be optionally recrystallized before entering in step (b). Recrystallization can be performed from the same solvent as used in the step (a) or from another solvent selected from the group consisting of esters, nitriles, ketones, ethers, chlorinated hydrogencarbons and $C_4$-$C_8$ alkyl alcohols or from a mixture thereof or from a mixture thereof with water. Preferred solvents used for said recrystallization are esters, nitriles, a mixture thereof or a mixture thereof with water. Most preferred solvent used for said recrystallization is a mixture of acetonitrile and water.

In a more preferred process according to the present invention giving excellent results, step (a) comprises the following sub-steps of:
(a1') dissolving crude perindopril in acetonitrile, preferably comprising a small amount of water, preferably up to 5% (w/w) of water, more preferably from 0.5 to 3.5% of water,
(a2') adding tert-octylamine, preferably at 40° C.,
(a3') cooling the obtained solution to a temperature below 10° C., preferably to 0° C., and
(a4') separating the obtained precipitate by filtration.

In a preferred first option (bi) of the process according to the present invention, step (b) comprises the following sub-steps of:
(bi1) dissolving the alkyl ammonium salt of perindopril obtained from step (a) in water or in an aqueous solution of sodium chloride,
(bi2) acidifying the obtained aqueous solution to a pH in which perindopril is in the free acid form, preferably by addition of at least one organic or mineral acid or a mixture thereof,
(bi3) extracting the obtained perindopril from the aqueous phase with an organic solvent,
(bi4) evaporating the said organic solvent,
(bi5) treating the obtained residue with an organic solvent, and
(bi6) separating the obtained precipitate by filtration and isolating crystalline perindopril.

Preferably in sub-step (bi2) is added a mixture comprising a $C_1$-$C_6$ alkanoic acid and strong mineral acid, more preferably a mixture comprising acetic acid and hydrochloric acid. Preferably from about 1 to about 4 equivalents, more preferably from about 1 to about 2 equivalents, most preferably from about 1.05 to about 1.15 equivalents of acid per starting alkyl ammonium salt of perindopril are added in step (bi2).

Optionally, the suspension obtained from sub-step (bi2) is heated to temperature from about 30° C. to about 50° C., preferably to about 35° C., in order to dissolve the alkyl ammonium salt of perindopril.

Preferably, the organic solvent used in step (bi3) is selected from the group consisting of esters, chlorinated hydrocarbons, ethers or aromatic hydrocarbons, more preferably the organic solvent used in step (bi3) is ethyl acetate or dichloromethane, most preferably dichloromethane.

Preferably, the organic solvent used in step (bi5) is selected from the group consisting of ethers or hydrocarbons, more preferably the organic solvent used in step (bi5) is diethylether or hexane, most preferably hexane.

In a more preferred first option (bi) of the process according to the present invention, step (b) comprises the following sub-steps of:
(bi1') dissolving perindopril tert-octylammonium salt obtained from step (a) in an aqueous solution of sodium chloride,
(bi2') acidifying the obtained aqueous solution to a pH in which perindopril is in the free acid form by the addition of a mixture of acetic acid and hydrochloric acid,
(bi3') extracting the obtained perindopril from the aqueous phase with dichloromethane,
(bi4') evaporating dichloromethane,
(bi5') treating the obtained residue with hexane and,
(bi6') separating the obtained precipitate by filtration and isolating crystalline perindopril.

In a preferred second option (bii) of the process according to the present invention, step (b) comprises the following sub-steps of:
(bii1) dissolving tert-octylammonium salt of perindopril obtained from step (a) in an organic solvent,
(bii2) removing tert-octylammonium cation from the obtained solution, and
(bii3) evaporating the said organic solvent to obtain crystalline perindopril.

Preferably in sub-step (bii1) tert-octylammonium salt of perindopril is dissolved in an organic solvent selected from the group consisting of alcohols, acetonitrile and ethyl acetate, preferably from isopropanol. Optionally, the obtained mixture is heated in order to completely dissolve the perindopril alkyl ammonium salt.

Preferably in sub-step (bii2) tert-octylammonium cation is removed from the solution obtained from sub-step (bii1) by precipitation thereof in the form of its insoluble salt, followed by filtering off. For this reason the solution obtained from sub-step (bii1) is treated with at least one acid, that generates in the used solvent an anion which forms with tert-octylammonium cation an insoluble salt. Preferably, the organic solvent used in sub-step (bii1) is selected from the group consisting of alcohol and ethyl acetate. Preferably the acid used in sub-step (bii2) is an inorganic acid. In a more preferred example, the organic solvent used in sub-step (bii1) is isopropanol and the acid used in sub-step (bii2) is sulfuric acid.

Preferably the acid is added at a temperature from about 30° C. to about 40° C. in sub-step (bii2).

In a more preferred second option (bii) of the process according to the present invention, step (b) comprises the following sub-steps of:
(bii1') dissolving tert-octylammonium salt of perindopril obtained from step (a) in an organic solvent,
(bii2') treating the obtained solution with at least one acid, followed by removing of the obtained insoluble tert-octylammonium salt, and
(bii3') evaporating the said organic solvent to obtain crystalline perindopril.

In a most preferred second option (bii) of the process according to the present invention, step (b) comprises the following sub-steps of:
(bii1") dissolving tert-octylammonium salt of perindopril obtained from step (a) in isopropanol,
(bii2") treating the obtained solution with sulfuric acid, followed by removing of the obtained insoluble tert-octylammonium sulfate,
(bii4") evaporating isopropanol to obtain crystalline perindopril.

The crystalline perindopril obtained by the manufacturing process of the present invention is highly pure, preferably having at least 99% of chromatographic purity, and can be used for the preparation of highly pure perindopril erbumine. Such pure perindopril erbumine has more than 99.6% of chromatographilc purity, preferably more than 99.8%. Processes for the preparation of perindopril erbumine from perindopril are known from the prior art.

A second object of the present invention is related to new alkyl ammonium salts of perindopril. Having checked tens of various metal and organic ammonium cations of perindopril it has surprisingly been found that only two salts of perindopril, besides perindopril tert-butylamine salt, were found to have satisfactory non-hygroscopic and well defined physical properties. These salts are perindopril neopentylammonium salt (i.e. perindopril 2,2-dimethylpropylammonium salt) and perindopril tert-octylammonium salt (i.e. perindopril 2,4,4-trimethyl-2-pentylammonium salt). Said new salts are obtained from step (a) according to the process of the present invention as previously described.

The new alkyl ammonium salts of perindopril according to the present invention are isolated in well defined crystalline states, suitable for easy handling. For instance the tert-octylammonium salt of perindopril expresses well defined melting point and has a powder x-ray diffraction pattern as depicted in FIG. 3 and shows the following characteristic 2θ angles:

| Angle 2θ (°) | Relative intensity (%) |
|---|---|
| 5.76 | 61.42 |
| 7.34 | 17.79 |
| 9.68 | 50.79 |
| 13.95 | 18.85 |
| 14.38 | 23.78 |
| 14.75 | 100.00 |
| 15.35 | 43.69 |
| 16.52 | 73.52 |
| 17.30 | 17.44 |
| 19.44 | 41.22 |
| 19.99 | 34.35 |
| 20.80 | 57.66 |
| 22.22 | 33.41 |
| 22.72 | 54.67 |
| 23.98 | 34.82 |
| 26.40 | 45.04 |
| 26.87 | 19.08 |

According to the process of the present invention the precipitation of the new alkyl ammonium salts of perindopril during step (a) allows to purify perindopril efficiently. The purification means that the resulted tert-octylammonium salt contains substantially less impurities than the starting material (i.e. the crude perindopril). An example of purification of perindopril by repeated crystallization of its tert-octylammonium salt from acetonitrile is represented in Example 3 and shown in Table 2 in which the improvement of chromatographic purity is from 72.5% to 99.8%.

New alkyl ammonium salts of perindopril according to the present invention may be used in a process of the preparation of perindopril erbumine of high purity, wherein, in first option, said salts are transferred to perindopril erbumine via crystalline perindopril according to the process of the present invention as previously described. In second option the solution of perindopril obtained from sub-steps (bi3), (bii2) or (bii2') is treated with the tert-butylamine to obtain perindopril erbumine by precipitation. In third option the solution of perindopril obtained from sub-steps (bi3), (bii2) or (bii2') is concentrated, obtained concentrate is diluted in an organic solvent, preferably in ethyl acetate, and obtained solution is treated with the tert-butylamine to obtain perindopril erbumine by precipitation.

Furthermore, new alkyl ammonium salts of perindopril are enough stable to be stored for a long time and may be used in pharmaceutical compositions.

In another embodiment the present invention is related to a process as described above, wherein in a further step the perindopril as obtained after step (b) or a new alkyl ammonium salts thereof as obtained after step (a), is formulated into a pharmaceutically acceptable dosage form, in particular wherein said dosage form is a tablet, pill, capsule or injectable.

Another object of the present invention is related to processes for the preparation of neopentylammonium salt of perindopril and/or tert-octylammonium salt of perindopril comprising the step (a) according to the process of the present invention as previously described.

Preferably a process for the preparation of neopentylammonium salt of perindopril comprises the following steps of:
(a1) dissolving crude perindopril in an organic solvent, or in a mixture of organic solvents, or in a mixture of organic solvent and water,
(a2) adding neopentylamine,
(a3) optionally cooling the obtained solution to temperature below 40° C., and
(a4) separating the obtained precipitate.

The details of steps (a1), (a2), (a3) and (a4) are already described above.

Preferably a process for the preparation of tert-octylammonium salt of perindopril comprises the following steps of:
(a1) dissolving crude perindopril in an organic solvent, or in a mixture of organic solvents, or in a mixture of organic solvent and water,
(a2) adding tert-octylamine,
(a3) optionally cooling the obtained solution to temperature below 40° C., and
(a4) separating the obtained precipitate.

The details of steps (a1), (a2), (a3) and (a4) are already described above.

More preferred process for the preparation of tert-octylammonium salt of perindopril comprises the following steps of:
(a1') dissolving crude perindopril in acetonitrile, preferably comprising a small amount of water, preferably up to 5% (w/w) of water, more preferably from 0.5 to 3.5% of water,
(a2') adding tert-octylamine, preferably at 40° C.,
(a3') cooling the obtained solution to a temperature below 10° C., preferably to 0° C., and
(a4') separating the obtained precipitate by filtration.

Another object of the present invention is related to pharmaceutical compositions comprising a therapeutically effective amount of neopentylammonium salt of perindopril, tert-octylammonium salt of perindopril or high pure crystalline perindopril having at least 99% of chromatographic purity, together with one or more pharmaceutically acceptable carriers or other excipients.

Another object of the present invention is related to pharmaceutical compositions comprising inclusion complexes of neopentylammonium salt of perindopril with cyclodextrins or their alkylated and hydroxyalkylated derivatives, inclusion complexes of tert-octylammonium salt of perindopril with cyclodextrins or their alkylated and hydroxyalkylated derivatives or inclusion complexes of high pure crystalline perindopril having at least 99% of chromatographic purity, with cyclodextrins or their alkylated and hydroxyalkylated derivatives together with one or more pharmaceutically acceptable carriers or other excipients. Preferably cyclodextrins or their alkylated and hydroxyalkylated derivatives are selected from the group consisting of α-, β-, γ- and ε-cyclodextrins or their methylated or hydroxypropylated derivatives, more preferably hydroxypropyl-β-cyclodextrin inclusion complexes are used.

A therapeutically effective amount of perindopril salt is the amount of perindopril salt which comprises an amount of perindopril which is appropriate in a dosage form useful to treat hypertension or cardiovascular diseases. In general, a pharmaceutically effective amount of perindopril is 1 to 15 mg of perindopril, preferably 2 to 8 mg.

Pharmaceutically acceptable excipients may be selected from the group consisting of binders, diluents, disintegrating agents, stabilizing agents, preservatives, lubricants, fragrances, flavoring agents, sweeteners and other excipients known in the field of the pharmaceutical technology. Preferably, carriers and excipients may be selected from the group consisting of hydroxypropylcellulose, lactose, microcrystalline cellulose, calcium carbonate, starch, colloidal silicone dioxide, sodium starch glycolate, talc, magnesium stearate, polyvinylpyrrolidone, and other excipients known in the field of the pharmaceutical technology.

Optionally, the pharmaceutical compositions of the invention may be combination products comprising one or more additional pharmaceutically active components in addition to perindopril. Preferably, an additional pharmaceutically active component is a diuretic, e.g. indapamide.

Suitable pharmaceutical compositions are solid dosage forms, such as tablets with immediate release or sustained release of the active principle, effervescent tablets, dispersion tablets and capsules.

The pharmaceutical compositions may be prepared by methods known in the field of the pharmaceutical technology.

Another object of the present invention is related to the use of neopentylammonium salt of perindopril, tert-octylammonium salt of perindopril or high pure crystalline perindopril having at least 99% of chromatographic purity for the preparation of a pharmaceutical composition for use in the treatment of cardiovascular diseases, e.g. hypertension or heart failure.

Another object of the present invention is related to a method for the treatment of cardiovascular diseases, e.g. hypertension or heart failure, comprising administering to a patient in need thereof a therapeutically effective amount of neopentylammonium salt of perindopril, tert-octylammonium salt of perindopril or high pure crystalline perindopril having at least 99% of chromatographic purity.

The following examples illustrate the invention, but do not limit it in any way:

EXAMPLE 1

Preparation of Crude Perindopril

Figure 1:
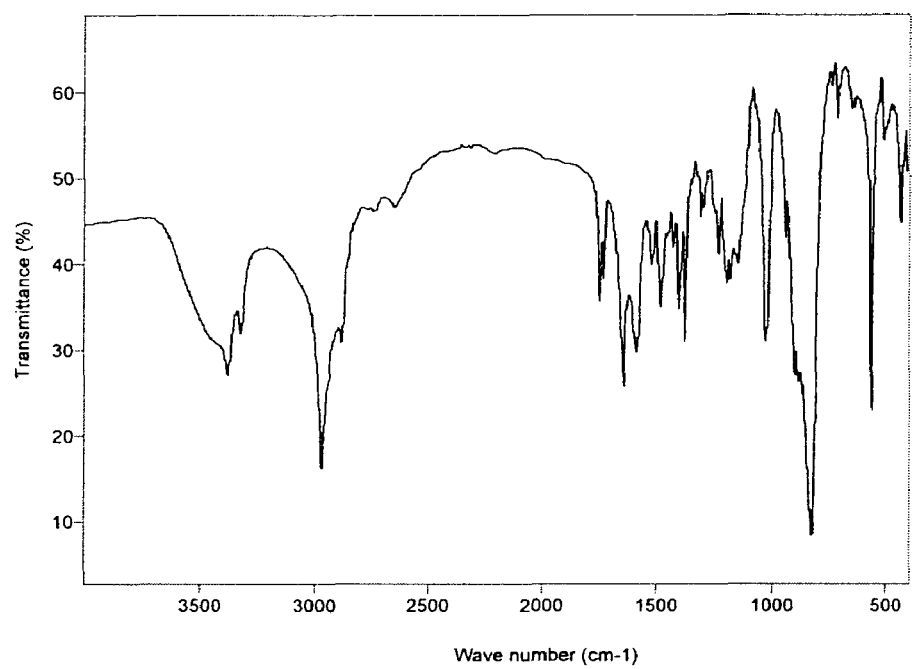
FIG. 1 represents IR spectrum of neopentylammonium salt of perindopril.

A mixture of 9.54 g of (2S,3aS,7aS)-2-carboxyperhydroindole benzyl ester, 7.26 g of N-((S)-1-carbetoxybutyl)-(S)-alanine and 12.7 g of O-(benzotriazol-1-yl)-N,N,N',N'-tetramethyluronium hexafluorophosphate in 225 ml of acetonitrile is stirred at room temperature for 30 min, then 560 ml of brine is added. The product is extracted twice with 400 ml of ethyl acetate, combined extracts are washed first with 800 ml of water, acidified with concentrated hydrochloric acid and then with 1.5 l of water. Organic phase is dried over anhydrous sodium sulphate and evaporated at 40° C. in vacuo to yield 13.5 g (88%) of benzyl (2S,3aS,7aS)-((2-(1-(ethoxycarbonyl)-(S)-butylamino)-(S)-propionyl)octahydroindole-2-carboxylate (benzyl ester of perindopril).

Crude benzyl ester of perindopril (13.5 g) is dissolved in 300 ml of methanol, to the obtained solution 1.35 g of catalyst (10% palladium on charcoal) is added. The mixture is stirred at room temperature under moderate flow of hydrogen for further 5 hours. The catalyst is then filtered off, washed with 50 ml of methanol and the solution is evaporated at 50° C. in vacuum. The residue is crude perindopril as a clear, colorless oily compound (72.5% area of perindopril).

EXAMPLE 2

Preparation of neopentylammonium salt of perindopril (2,2-dimethylpropylammonium (2S,3aS,7aS)-((2-(1-(ethoxycarbonyl)-(S)-butylamino)-(S)-propionyl)octahydro-indole-2-carboxylate)

2.85 g of crude perindopril obtained from example 1 is dissolved in 30 ml of ethyl acetate, the solution is then heated to 35° C. following by adding 2.4 ml of neopentylamine. The mixture is cooled to −10° C. and after 24 h the precipitate is filtered off and dried. 2.23 mg (63%) of neopentylammonium salt of perindopril is obtained.

Melting point: 80-130° C. (deg)-Kofler microstage, 85° C. (onset, DSC)

Figure 2:
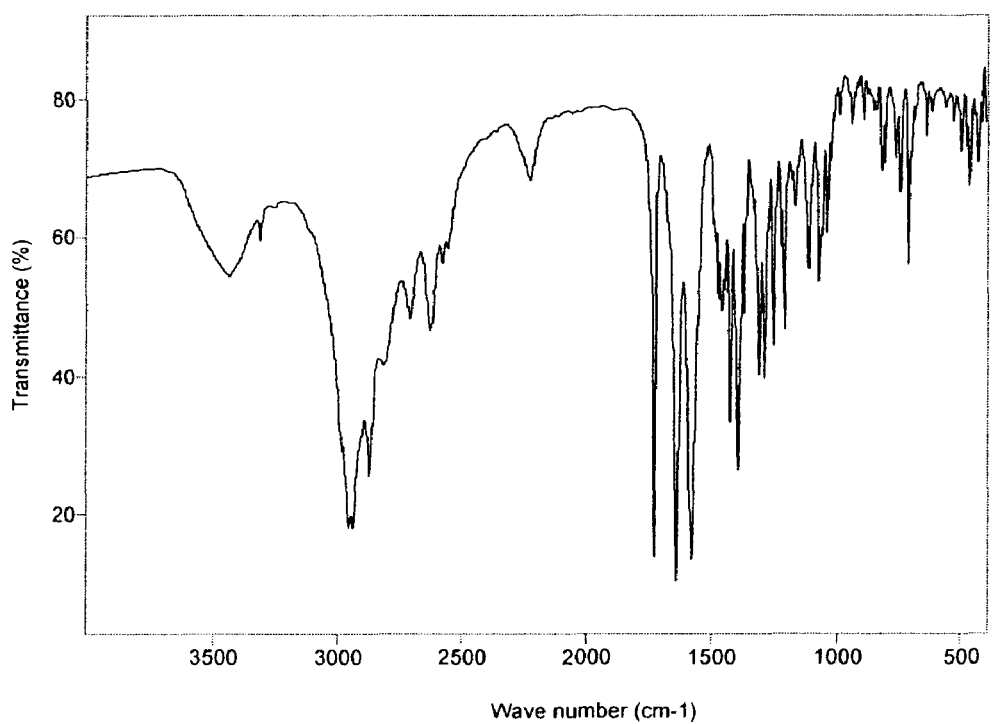
FIG. 2 represents IR spectrum of tert-octylammonium salt of perindopril.

IR spectrum is depicted in FIG. 2

EXAMPLE 3

Preparation of tert-octylammonium salt of perindopril (2,4,4-trimethyl-2-pentylammonium (2S,3aS,7aS)-((2-(1-(ethoxycarbonyl)-(S)-butylamino)-(S)-propionyl)octahydro-indole-2-carboxylate)

26.3 g of crude perindopril obtained from example 1 is dissolved in 300 ml of acetonitrile, the solution is then heated to 40° C. following by adding 21 ml of tert-octylamine. As soon as the first crystals began to crystallize 2.5 ml of water is added and the mixture is heated to the reflux temperature in order to redissolve crystals. The solution is then cooled to 0° C. and after 4 h the precipitated tert-octylammonium salt is filtered off and dried. 21 g (59%) of crude salt is obtained and further crystallized from mixture of 300 ml acetonitrile and 10 ml of water to yield 17.8 g of crystalline pure salt (85% yield of recrystallization).

Melting point: 154° C. (deg)-onset, DSC

IR spectrum is depicted in FIG. 2

Figure 3:
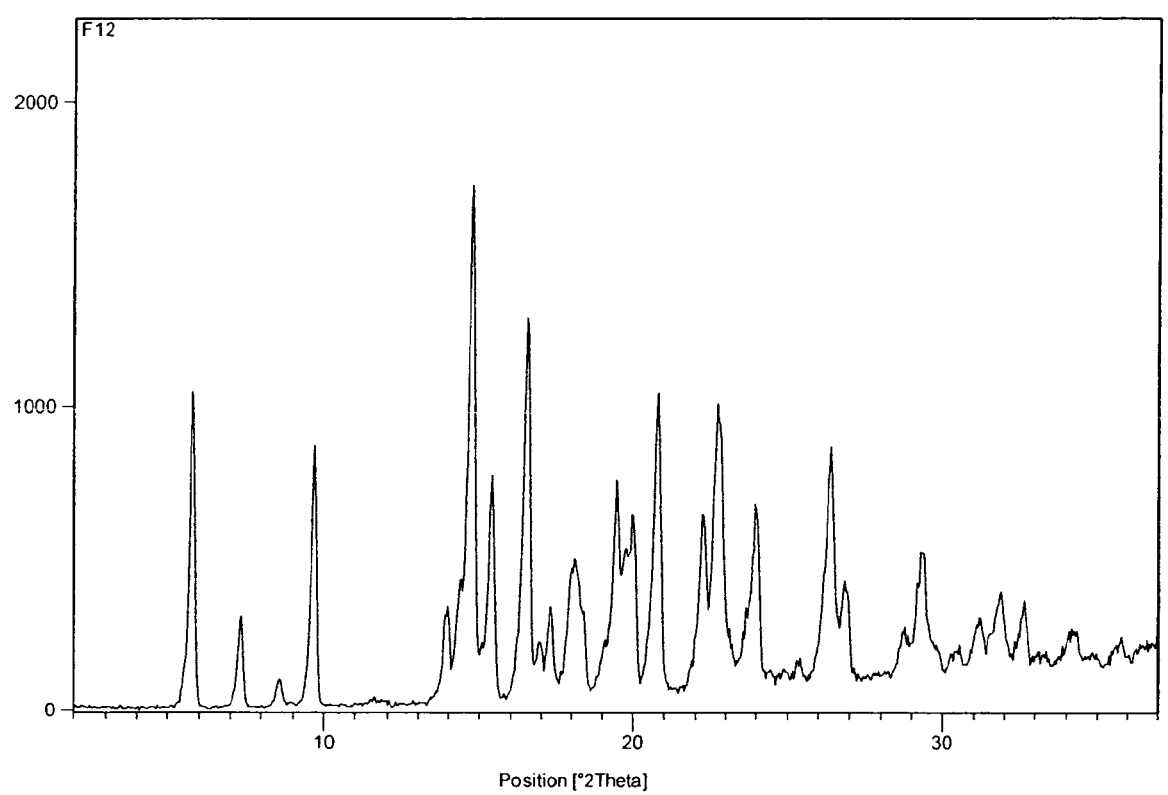
FIG. 3 represents X-ray diffraction diagram of the tert-octylammonium salt of perindopril.

X-Ray Powder diffraction pattern is represented in FIG. 3 and shows the following characteristic 2θ angles (Table 1):

TABLE 1

| Angle 2θ (°) | Relative intensity (%) |
|---|---|
| 5.76 | 61.42 |
| 7.34 | 17.79 |
| 9.68 | 50.79 |
| 13.95 | 18.85 |
| 14.38 | 23.78 |
| 14.75 | 100.00 |
| 15.35 | 43.69 |
| 16.52 | 73.52 |
| 17.30 | 17.44 |
| 19.44 | 41.22 |
| 19.99 | 34.35 |
| 20.80 | 57.66 |

TABLE 1-continued

| Angle 2θ (°) | Relative intensity (%) |
|---|---|
| 22.22 | 33.41 |
| 22.72 | 54.67 |
| 23.98 | 34.82 |
| 26.40 | 45.04 |
| 26.87 | 19.08 |

Table 2 shows a degree of purification of perindopril throughout the process of Example 3 given in chromatographic purity (area %).

TABLE 2

|  | chromatographic purity (% area) |
|---|---|
| Crude perindopril | 72.5 |
| Crude tert-octylammonium salt of perindopril | 98.7 |
| Crystallized tert-octylammonium salt of perindopril | 99.8 |

EXAMPLE 4

Preparation of Tert-Octylammonium Salt of Perindopril 13.6 g of perindopril obtained from example 1 (91% contain) is dissolved in 200 ml of acetonitrile and 1.25 ml of water is added under stirring. The solution is then heated to 40° C. following by adding 8.0 ml of tert-octylamine and further slow heating to reflux and final cooling to 0° C. After 6 h at 0° C. precipitated crystals are filtered off and dried to yield 13.1 g of salt (78%).

EXAMPLE 5

Preparation of pure perindopril ((2S,3aS,7aS)-((2-(1-(ethoxycarbonyl)-(S)-butylamino)-(S)-propionyl) octahydroindole-2-carboxylic acid) from tert-octylammonium salt of perindopril 8.11 g of tert-octylammonium salt of perindopril obtained from example 4 is suspended in 100 ml of isopropanol, the mixture is heated to 60° C. to obtain solution which is further cooled to 25° C. and 936 mg of sulfuric acid (96%, d=1.84) is added drop-wise. The obtained mixture is stirred for 30 min at room temperature and the precipitate is filtered off. The filtrate is evaporated to dryness below 45° C., the residue is triturated with 15 ml of diisopropyl ether and again evaporated to dryness. The trituration is repeated twice to obtain a viscous mass, which is dried for 30-60 min at room temperature in high vacuum to give 6.0 g (100%) of pure perindopril as solid glassy material (contain 97%).

EXAMPLE 6

Preparation of Crystalline Perindopril from Tert-Octylammonium Salt of Perindopril 994 mg tert-octylammonium salt of perindopril obtained from example 4 is suspended in 32 ml of 10% NaCl solution, then 0.56 ml of acetic acid and 0.30 ml of conc. HCl/water 1:1 mixture. The suspension is heated to 35° C. for 10 min in order to dissolve the salt and the resulted solution is extracted twice with 20 ml of dichloromethane. Combined extracts are rewashed twice with 40 ml 10% NaCl solution. Dichloromethane is finally removed by evaporation, the residue is treated with 10 ml of hexane, the mixture is stirred for 5 hours and the solid material is filtered off to give 655 mg of crystalline perindopril (99.1%).

EXAMPLE 7

Preparation of Perindopril Erbumine from Tert-Octylammonium Salt of Perindopril 5.0 g of tert-octylammonium salt of perindopril obtained from example 4 is dissolved in a 150 ml of ethyl acetate and 3 ml of water, the mixture is heated to the reflux to obtain solution which is further cooled to 55° C. and 564 mg of sulfuric acid (96%, d=1.84) is added drop-wise. The obtained suspension is cooled to room temperature and the precipitated sulfate is filtered off. The filtrate is evaporated to dryness below 45° C. and the residue is dried in high vacuum (below 1 mbar) to obtain 3.55 g of crude perindopril 1.49 g of the residue (perindopril-97.96 area %)) is dissolved in 18 ml of ethyl acetate and 1.0 ml of tert-butylamine is added. The mixture is heated to the reflux, hot solution is filtered under pressure and cooled to the room temperature. The precipitate is filtered off and dried in vacuo to yield 1.12 g of perindopril erbumine (99.83 area %)

Analytical Data in Examples were Achieved by the Following Hardware:

Melting points were determined in Kofler hot stage microscope and differential dynamic calorimeter Mettler Toledo DSC822e IR spectra were analyzed in KBr on Nicolet Nexus FTIR spectrophotometer Powder X-ray diffraction spectra of the sample was recorded on Siemens D-5000 with reflexion technique: CuKα radiation, range from 20 to 37° 2θ, step 0.04° 2θ, integration time 1 sec.

Chromatographic Conditions:

Mobile Phase:

A: disolve 0.92 g of sodium heptansulphonate in 1000 ml of water, add 1 ml of triethylamine and adjust to pH 2.0 with a mixture of perchloric acid and water B: acetonitrile Column: C8, 4 μm, pore size of 6 nm, 250×4,0 mm (Merck Supersphere 60 RP-8)

Temperature: 70° C.

Flow rate: 1.5 ml/min

Wavelength: 215 nm

Injection volume: 20 μl

Gradient table:

| t | % A | % B |
|---|---|---|
| 0 | 73 | 27 |
| 8 | 73 | 27 |
| 25 | 40 | 60 |
| 30 | 40 | 60 |
| 40 | 20 | 80 |
| 45 | 0 | 100 |
| 50 | 73 | 27 |

Equipment: Waters Alliance 2695 separations module, detector PDA 2996, software Empower 5.0

The invention claimed is:
1. The tert-Octylammonium salt of perindopril.
2. Crystalline tert-octylammonium salt of perindopril comprising the following powder x-ray diffraction pattern:

| Angle 2.θ (°) | Relative intensity (%) |
|---|---|
| 5.76 | 61.42 |
| 7.34 | 17.79 |
| 9.68 | 50.79 |
| 13.95 | 18.85 |
| 14.38 | 23.78 |
| 14.75 | 100.00 |
| 15.35 | 43.69 |
| 16.52 | 73.52 |
| 17.30 | 17.44 |
| 19.44 | 41.22 |
| 19.99 | 34.35 |
| 20.80 | 57.66 |
| 22.22 | 33.41 |
| 22.72 | 54.67 |
| 23.98 | 34.82 |
| 26.40 | 45.04 |
| 26.87 | 19.08. |

3. The Neopentylammonium salt of perindopril.

* * * * *